(12) United States Patent
Chantranukul et al.

(10) Patent No.: US 7,494,667 B2
(45) Date of Patent: Feb. 24, 2009

(54) BLENDS OF DIFFERENT ACYL GELLAN GUMS AND STARCH

(75) Inventors: Arjnarong Chantranukul, Bangkok (TW); Chaodong Xiao, East Hanover, NJ (US); Zhixin Li, Bridgewater, NJ (US); Sibu Chakrabarti, Randolph, NJ (US); Monika K. Okoniewska, Princeton, NJ (US)

(73) Assignee: Brunob II B.V. (NL)

( * ) Notice: Subject to any disclaimer, the term of this patent is extended or adjusted under 35 U.S.C. 154(b) by 688 days.

(21) Appl. No.: 10/791,478

(22) Filed: Mar. 2, 2004

(65) Prior Publication Data

US 2005/0196436 A1 Sep. 8, 2005

(51) Int. Cl.
*A61K 9/48* (2006.01)
*A23L 1/05* (2006.01)

(52) U.S. Cl. .................................. 424/451; 426/573
(58) Field of Classification Search ............. 424/451; 426/573
See application file for complete search history.

(56) References Cited

U.S. PATENT DOCUMENTS

| | | | |
|---|---|---|---|
| 4,306,059 A | 12/1981 | Yokobayashi et al. | |
| 4,326,053 A | 4/1982 | Kang et al. | |
| 4,385,123 A | 5/1983 | Kang et al. | |
| 4,576,284 A | 3/1986 | Wittwer et al. | |
| 4,591,475 A | 5/1986 | Tomka et al. | |
| 4,673,438 A | 6/1987 | Wittwer et al. | |
| 4,738,724 A | 4/1988 | Wittwer et al. | |
| 4,869,916 A | 9/1989 | Clark et al. | |
| 4,956,193 A | 9/1990 | Cais et al. | |
| 5,089,307 A | 2/1992 | Ninomiya et al. | |
| 5,095,054 A | 3/1992 | Lay et al. | |
| 5,112,445 A | 5/1992 | Winston, Jr. et al. | |
| 5,190,927 A * | 3/1993 | Chang et al. | 514/54 |
| 5,342,626 A * | 8/1994 | Winston et al. | 424/461 |
| 5,620,757 A | 4/1997 | Ninomiya et al. | |
| 5,756,123 A | 5/1998 | Yamamoto et al. | |
| 6,210,709 B1 | 4/2001 | Laba et al. | |
| 6,214,376 B1 | 4/2001 | Gennadios | |
| 6,303,290 B1 * | 10/2001 | Liu et al. | 435/4 |
| 6,340,473 B1 | 1/2002 | Tanner et al. | |
| 6,344,346 B1 | 2/2002 | Alami et al. | |
| 6,375,981 B1 * | 4/2002 | Gilleland et al. | 424/452 |
| 6,475,542 B1 | 11/2002 | Soeda et al. | |
| 6,517,865 B2 | 2/2003 | Cade et al. | |
| 6,528,088 B1 | 3/2003 | Gilleland et al. | |
| 6,582,727 B2 | 6/2003 | Tanner et al. | |
| 6,635,275 B1 | 10/2003 | Scott et al. | |
| 6,649,188 B2 | 11/2003 | Gilleland et al. | |
| 2003/0072731 A1 | 4/2003 | Gulian et al. | |
| 2003/0211146 A1 | 11/2003 | Scott et al. | |
| 2004/0052839 A1 | 3/2004 | Archibald et al. | |
| 2004/0071808 A1 | 4/2004 | Peter et al. | |
| 2004/0102328 A1 | 5/2004 | Johnson et al. | |
| 2004/0105835 A1 | 6/2004 | Scott et al. | |
| 2005/0069579 A1 | 3/2005 | Kamaguchi et al. | |
| 2005/0084516 A1 | 4/2005 | Ballard et al. | |

FOREIGN PATENT DOCUMENTS

| | | |
|---|---|---|
| EP | 0 547 551 | 6/1993 |
| EP | 0404582 | 6/1994 |
| EP | 1 103 254 | 5/2001 |
| EP | 1104652 | 6/2001 |
| EP | 1 186 626 | 3/2002 |
| EP | 1 249 219 | 10/2002 |
| EP | 1447082 | 8/2004 |
| GB | 2 343 669 | 5/2000 |
| JP | 20030551 | 2/2003 |
| WO | WO 95/34269 | 12/1995 |
| WO | WO 98/42316 | 10/1998 |
| WO | WO 00/10538 | 3/2000 |
| WO | WO 00/18835 | 6/2000 |
| WO | WO 01/03677 | 1/2001 |
| WO | WO 01/37817 | 5/2001 |
| WO | WO 01/91721 | 12/2001 |
| WO | WO 01/92400 | 12/2001 |
| WO | WO 01/92401 | 12/2001 |
| WO | WO0238132 | 5/2002 |
| WO | WO0309832 | 2/2003 |

OTHER PUBLICATIONS

Krochta, John M. and Catherine De Mulder-Johnston, "Edible and Biodegradable Polymer Films: Challenges and Opportunities", Food Technology, vol. 51, No. 2: 61-74, 1997.
Miyoshi, E. and K. Nishinari, "Rheological and thermal properties near the sol-gel transition of gellan gum aqeous solutions", Prog Colloid Polym Sci 114: 68-82, 1999.
Miyoshi, E. and K. Nishinarl, "Effects of sugar on the sol-gel transition in gellan gum aqeous solutions", Prog Colloid Polym Sci 114: 83-91, 1999.
Vemuri, Sriram, "Measurement of soft elastic gelatin capsule firmness with a universal testing machine", Drug Development and Industrial Pharmacy, 10 (3): 409-423, 1984.

* cited by examiner

*Primary Examiner*—M. P. Woodward
*Assistant Examiner*—Aradhana Sasan

(57) ABSTRACT

The present invention relates to a method of producing a film forming blend of different acyl gellan gums with starch having similar textural and functional properties compared to gelatin. Films prepared using such blends have a high modulus and excellent strength and elongation. The present invention also relates to soft capsules prepared using such blends or films, which have good sealability.

17 Claims, No Drawings

BLENDS OF DIFFERENT ACYL GELLAN GUMS AND STARCH

BACKGROUND OF THE INVENTION

The present invention relates to a method of producing a blend of different acyl gellan gums with starch and a plasticizer having similar textural and functional properties compared to gelatin. The present invention also relates to a method of making films and soft capsules prepared using such blends and the method of making such films and capsules.

Gelatin is used in various pharmaceutical applications including soft gelatin capsules and hard gelatin capsule shells as well as many different food applications. Soft capsules are used to encapsulate a solution or dispersion, for example of a nutritional or pharmaceutical active agent, in a liquid carrier and have many advantages over other dosage forms, permitting accurate delivery of a unit dose in an easy-to-swallow, transportable, essentially tasteless form.

However, gelatin has many drawbacks, including the cost and continuity of a safe supply. Bovine sources are also undesirable to certain individuals, such as vegetarians and those wishing to maintain Kosher or Halal standards. Further, gelatin is prone to crosslinking, caused by aging or due to reaction with compounds such as aldehydes, which reduces its solubility in gastric juices.

Gelatin provides good sealing of the capsule at a temperature above the melting point of the film, a wet film strong enough to survive the manipulation in the encapsulation machine, dissolution in gastric juices, and sufficient elasticity to allow formation of a capsule. With the growing concern of Bovine Spongiform Encephilitis (BSE) disease in products derived from cows, many attempts have been made to replace gelatin, such as the 25-45% present in soft capsules. However, these approaches have typically failed in that the resultant products had unacceptably different textural and/or functional properties.

Surprisingly, it has now been found that the use of a film forming blend of different acyl gellans with starch provides an excellent wet film with a high modulus and excellent strength and elongation. Further, soft capsules made with such blends or films have good sealability.

SUMMARY OF THE INVENTION

The present invention relates to a method of producing a film forming blend of different acyl gellan gums with starch and a plasticizer having similar textural and functional properties compared to gelatin and can be used as a replacement thereof. Films prepared using such blends have a high modulus and excellent strength and elongation. The present invention also relates to soft capsules prepared using such blends or films, which have good sealability.

Gellan gum, as used herein, refers to the extracellular polysaccharide obtained by the aerobic fermentation of the microorganism *Pseudomonas elodea* in a suitable nutrient medium. Various forms of gellan gum have been described in the art and may be used in the present invention.

On a wet basis, as used herein, is intended to mean at 50% (wt/wt) solids.

Capsule shells, as used here, is intended to mean the capsule without the fill material.

DETAILED DESCRIPTION OF THE INVENTION

The present invention relates to a method of producing a film-forming blend of different acyl gellan gums with starch and a plasticizer having similar textural and functional properties compared to gelatin. Films prepared using such blends have a high modulus and excellent strength and elongation. The present invention also relates to soft capsule shells prepared using such blends or films, which have good sealability.

The blend of the present invention comprises at least two gellan gums with different acyl contents, one having a high acyl content and one having a low acyl content. As used herein, high acyl content is intended to mean more than 40% acetyl and more than 45% glyceryl residual substituents per repeat unit. As used herein, low acyl content is intended to mean less than 25% acetyl and less than 15% glyceryl residual substituents per repeat unit.

The high acyl gellan is used to increase the elasticity and is suitably present in an amount of from about 0.3 to 5% by weight of the composition on a wet basis. In another embodiment, the high acyl gellan is present in an amount of about 0.5 to 5% by weight of the composition on a wet basis. The low acyl gellan is used to increase the rigidity and is suitably present in an amount of from about 0.1 to 4% by weight of the composition on a wet basis. In another embodiment, the low acyl gellan is present in an amount of about from about 0.1 to 2% by weight of the composition on a wet basis. In one embodiment, the ratio (wt/wt) of high acyl gellan to low acyl gellan is at least about 0.25 to 1.0 and no more than about 30.0 to 1.0. The gellan blend may be used in any amount necessary to achieve the desired gel strengthening effect, both modulus and strength and in one embodiment is used in an amount of about 0.4 to 10% by weight of the composition on a wet basis. Alternately, the gellan blend may be used in an amount of about 1 to 5%, by weight of the composition on a wet basis. The gellan is also present to allow heat reversibility of the system, which may be enhanced by decreasing the amount of low acyl gellan to the lower end of the range.

The blend also comprises at least one starch. Starch, as used herein, is intended to include all starches derived from any native source, any of which may be suitable for use herein. A native starch as used herein, is one as it is found in nature. Also suitable are starches derived from a plant obtained by standard breeding techniques including crossbreeding, translocation, inversion, transformation or any other method of gene or chromosome engineering to include variations thereof. In addition, starch derived from a plant grown from artificial mutations and variations of the above generic composition, which may be produced by known standard methods of mutation breeding, are also suitable herein.

Typical sources for the starches are cereals, tubers, roots, legumes and fruits. The native source can be any variety of corn (maize), pea, potato, sweet potato, banana, barley, wheat, rice, oat, sago, amaranth, tapioca, arrowroot, canna, sorghum, and waxy and high amylose varieties thereof. As used herein, "waxy" is intended to include a starch containing no more than about 10%, particularly no more than about 5%, more particularly no more than about 3%, and most particularly no more than about 1% amylose by weight. As used herein, the term "high amylose" is intended to include a starch containing at least about 40%, particularly at least about 70%, more particularly at least about 80% by weight amylose. As used herein, the term "amylose-containing" is intended to include a starch containing at least about 10% by weight amylose. In one embodiment, suitable starches are those which are amylose containing starches, in another amylose containing starches which are not high amylose.

The starches may be pregelatinized using techniques known in the art and disclosed for example in U.S. Pat. Nos. 4,465,702, 5,037,929, 5,131,953, and 5,149,799. Also see, Chapter XXII—"Production and Use of Pregelatinized Starch", *Starch: Chemistry and Technology*, Vol. III—Industrial Aspects, R. L. Whistler and E. F. Paschall, Editors, Academic Press, New York 1967.

The starch may be a native starch, or a modified starch. Modified starch, as used herein, is intended to include starches which have been modified physically, chemically and/or by hydrolysis. Physical modification includes by shearing or thermally-inhibition, for example by the process described in U.S. Pat. No. 5,725,676.

The starch may be chemically modified, including without limitation, crosslinked, acetylated, organically esterified, hydroxyethylated, hydroxypropylated, phosphorylated, inorganically esterified, cationic, anionic, nonionic, and zwitterionic, and succinate and substituted succinate derivatives thereof. Such modifications are known in the art, for example in *Modified Starches: Properties and Uses*, Ed. Wurzburg, CRC Press, Inc., Florida (1986).

The starches may be hydrolyzed, and suitable starches include fluidity or thin-boiling starches prepared by oxidation, acid hydrolysis, enzyme hydrolysis, heat and or acid dextrinization. These processes are well known in the art.

Any starch having suitable properties for use herein may be purified by any method known in the art to remove starch off flavors and colors that are native to the polysaccharide or created during processing. Suitable purification processes for treating starches are disclosed in the family of patents represented by EP 554 818 (Kasica, et al.). Alkali washing techniques, for starches intended for use in either granular or pregelatinized form, are also useful and described in the family of patents represented by U.S. Pat. No. 4,477,480 (Seidel) and U.S. Pat. No. 5,187,272 (Bertalan et al.).

Suitable starches in the present invention include those which are stabilized, including hydroxyalkylated starches such as hydroxypropylated or hydroxyethylated starches, and acetylated starches. Also suitable are dextrinized starches. In one embodiment, these starches will have a low viscosity, with a water fluidity in the range of from about 20 to 90. In another embodiment, the starches will have a water fluidity in the range of about 65 to 85. Water fluidity is known in the art and, as used herein, is measured using a Thomas Rotational Shear-type Viscometer (commercially available from Arthur A. Thomas Co., Philadelphia, Pa.), standardized at 30° C. with a standard oil having a viscosity of 24.73 cps, which oil requires 23.12±0.05 sec for 100 revolutions. Accurate and reproducible measurements of water fluidity are obtained by determining the time which elapses for 100 revolutions at different solids levels depending on the starch's degree of conversion: as conversion increases, the viscosity decreases. The conversion may be by any method known in the art including oxidation, enzyme conversion, acid hydrolysis, heat and/or acid dextrinization.

The starch may be used in any amount necessary to achieve the desired viscosity and film thickness. In one embodiment, the starch will be used in an amount of about 15 to 40%, in another about 20 to 35%, by weight of the composition on a wet basis. In one embodiment, the starch is added, on a dry weight basis, at a ratio of at least about 6 to 1, and no more than about 60 to 1, by weight of the total gellan.

The blend further includes at least one plasticizer. The plasticizer used will depend in part upon the end use application and is intended to include polyhydric alcohols such as glycerin, sorbitol, maltitol, propylene glycol, and polyethylene glycol, saccharides and polysaccharide. In one suitable embodiment, the plasticizers include glycerin and sorbitol. The plasticizer may be used in any amount necessary to achieve the desired plasticizing effect. In one embodiment, the plasticizer will be used in an amount of about 10 to 25%, in another at about 13 to 22%, by weight of the composition on a wet basis. The plasticizer is typically added at a dry weight level of about 30 to 80% by weight of the starch.

In another embodiment, hydrophilic or surface hydrophilically modified colloidal particles are added. Such particles include, without limitation, cellulose crystal particles and silicone particles, such as silicon dioxide. In one embodiment, the particles are colloidal silicon dioxide. These particles may be used in any amount necessary to achieve the desired film strength and to reduce the drying time of the film and improve the powder flow of the blend. In one embodiment, the particles are present in an amount of about 0.5 to 10%, in another at about 0.5 to 5%, by weight of the composition on a wet basis. The hydrophilic or surface hydrophilically modified colloidal particles are added, on a dry weight basis, at a ratio of at least about 0.2 to 1.0, and no more than about 5.0 to 1.0, by weight of the gellan blend.

Other additives may optionally be included in the film as is common in the industry as long as they do not adversely affect the film, including without limitation colors, flavors, preservatives, opacifying agents, embrittlement inhibiting agents, disintegrants and buffers. However, the blends are preferably essentially gelatin-free. In one embodiment, the blend contains less than 0.1% gelatin, in another less than 0.05% gelatin, and in a further embodiment no gelatin.

The blend is advantageous in that it has a hot liquid viscosity suitable for casting on the drum of a rotary die, a process known in the art for producing soft capsule shells. In one embodiment, suitable blends will have a hot viscosity of from about 2,000 to about 100,000 centipoise, in another from about 4000 to 40,000 centipose, at a solid concentration of from about 30 to 70% and a temperature of about 60 to 100° C.

The dry blend is added to water to form a solid concentration suitable for the film or capsule shell process used. For casting of a hot liquid on a cold drum, the concentration is typically suitable at about 30 to 70% solids. Other methods known in the art for forming a film may be used including without limitation extrusion, either direct or from pre-made pellets. The film may be made during the encapsulation process or may be pre-made for later use.

The resultant wet film has a modulus of about 5 to 200 kPa. In another embodiment, the wet film modulus is about 10 to about 250 kPa. Modulus, as used herein, is defined as film stress per unit elongational strain measured by Texture Analyzer TA-XT2 using a speed of 2 mm/s. The films are typically cooled down to room temperature from film casting temperature around 60-95° C. and before significantly lost of moisture.

The film also has a wet strength of about 10 to about 1000 kPa. In another embodiment, the wet strength is about 20 to about 500 kPa. Wet strength, as used herein, is defined as area of a stress/strain curve for an elongation test, where strain is a unitless percentage.

The film further has a dry modulus of about 0.5 to about 50 MPa. In another embodiment, the dry modulus is about 1 to about 20 MPa. Dry modulus, as used herein, is defined as the modulus of a film that is dried at 50% RH for more than 12 hours. The film has a dry strength of about 0.1 to about 100 Mpa. In another embodiment, the dry strength is from 0.2 to 50 MPa. The wet film typically has an elongation at break of about 50% to about 500%, and the dry film typically has a elongation at break of about 20% to about 150%.

The film's attributes allow it to be used to form essentially gelatin-free capsule shells using techniques known in the art, including on a rotary machine. The soft capsule shells have the same excellent properties as the film and excellent sealability. In some embodiments, the capsule shells can be sealed at moisture contents of about 20 to 60% by weight at a temperature of above about 40-95° C. In further embodiments, the capsule shells can be sealed at moisture contents of about 30 to 55% by weight at the same temperatures. In alternate embodiments, the sealing temperatures are in the range of 45 to 75° C. Excellent seal, as used herein, is intended to mean a seal which will withstand further processing and transportation of the capsule such that it reaches the consumer without leaks or tears.

Capsule shells made using the rotary die process will be similar in look and feel to gelatin capsule shells, having a wet thickness of about 0.25 to 1.8 mm, in another embodiment about 0.6 to 1.4 mm. The fill materials for the soft capsule shells may be any of those typically used in the art, including oils, hydrophobic liquids and emulsions containing active agents. Fill materials may include cosmetics, bath oils, foods, vitamins, detergents, liquids, semisolids, suspensions, flavorings and pharmaceuticals. After filling, the capsules may be dried using techniques conventional in the art, including tray drying.

EXAMPLES

The following examples are presented to further illustrate and explain the present invention and should not be taken as limiting in any regard. All percents used are on a weight basis.

The following viscosity measurement is used throughout the examples:

A steam bath cooked solution is immediately poured into a preheated (to 90° C.) thermal cell. The solution temperature was then allowed to stabilize at 90° C. The static viscosity was measured using Brook Field Viscometer DV-II+, and spindle number 21 or 27.

The following ingredients are used throughout the examples.

Starch A, a hydroxypropylated corn starch with water fluidity of 80.

Starch B, a hydroxypropylated waxy corn starch with water fluidity of 60.

Starch C, a hydroxypropylated waxy corn starch, cold water soluble, with water fluidity of 75.

Starch D, a highly degraded waxy corn starch.

Starch E, a hydroxypropylated tapioca starch with water fluidity of 40.

Starch F, a hydroxypropylated waxy starch with water fluidity of 70.

Starch G, a hydroxypropylated waxy starch with water fluidity of 65.

KELCOGEL LT 100, a high acyl gellan gum commercially available from CP Kelco (Wilmington, Del.).

KELCOGEL F, a low acyl gellan gum commercially available from CP Kelco (Wilmington, Del.).

AEROSIL 200, a silica filler commercially available from Degussa (Akron, Ohio).

AVICEL PH101, a micro crystalline cellulose particle commercially available from FMC (Philadelphia, Pa.)

Glycerin, commercially available from Aldrich (Milwaukee, Wis.).

Sorbitol, commercially available from Aldrich (Milwaukee, Wis.).

Example 1

Preparation of the Blend a. A powder blend was premixed with 1.5 g of KELCOGEL LT100, 1 g of KELCOGEL F, 1 g of AEROSIL 200, and 30 g of starch A.

The powder mixture was added into a beaker containing 18 g of glycerin dissolved in 48.5 g distilled water. The total mixture was blended to form a thick paste.

The paste was then cooked under agitation at around 90° C.-100° C. using a steam bath for 1-2 hours until the solution became smooth, close to transparent. The final viscosity was 30,000-50,000 centipoise.

b. Example 1a was repeated except no AEROSIL was used and the water was in an amount of 49.5. The finished viscosity and wet film strength were slightly decreased from 1a.

c. Example 1a was repeated except the starch A is replaced with starch E. The finished viscosity was 70,000 cPs. The wet film strength was slight higher than that of 1a.

d. Example 1a was repeated except glycerin was used in an amount of 13 g and distilled water in an amount of 53.5 g. The resultant viscosity was similar to that of 1a and the dry film had a higher modulus and less elongation than that of 1a.

e. Example 1a was repeated except 15 g of sorbitol were used in place of glycerin, and distilled water was used in an amount of 51.5 g. The resultant viscosity was similar to that of 1a.

f. Example 1a was repeated except the amounts of KELCOGEL LT 100, KELCOGEL F were 2 g and 0.5 g. The solution viscosity was increased, the wet film strength was increased, and the sealability was improved compared to 1a.

g. Example 1a was repeated except the amount of starch and water were 45 g and 33.5 g, respectively. The viscosity was around 15,000 cps and the wet film strength was improved from 1a.

h. Example 1a was prepared except 3 g of AVICEL PH 101 was used in place of AEROSIL and the amount of water used was 46.5 g. The solution viscosity was slightly increased and the wet film strength was improved from 1a.

i. Example 1a was repeated except sodium chloride was added to the water-glycerin mixture to result in a final paste with 100 milli Molar concentration of sodium chloride. The wet film strength was improved from 1a.

j. Example 1a was repeated except calcium nitrate was added to the water-glycerin mixture to result in a final paste with 10 milliMolar concentration of calcium nitrate. The wet film strength was improved from 1a.

k. Example 1a was repeated except KELCOGEL F was replaced with guar gum. The wet film strength was decrease from 1a. The example was then repeated using agar instead of the guar gum and the wet film strength was also decreased.

l. Example 1a was prepared except the amount water was 60 g. The solution viscosity was around 5000 cps. The wet film strength was decreased. Further drying of the film was needed in order to seal the capsules.

Example 2

Preparation of Films

The finished solutions from example 1 were allowed to quickly degas while maintaining the temperature, and a film was cast onto a glass or metal substrate covered with a thin layer of vegetable oil or other release agent, using a film drawer with 0.6-1.4 mm gap.

Each wet film was sampled right after the film was cooled down to room temperature, around 22.5° C. A dry film was sampled after drying for at around 24 hours at 22.5° C. and 50% RH.

Example 3

Mechanical Testing

The film samples were cut into 20 mm wide and 55 mm long. These films, after clamping onto Texture Analyzer TA-XT2, gave an initial film length of 20 mm. They were then stretched at a constant rate of 2 mm/minutes until break. The stress was measured with a 5 kg Texture Analyzer transducer. The stress-strain curves were recorded automatically.

Modulus was calculated as the maximum strength divided by the elongation at the break. The film strength was calculated by integrating the area underneath the stress-strain curves.

Example 4

Mechanical Properties

Example 1a was measured with results of a wet film modulus of 28 kPa, and a wet film strength 98 kPa, and a wet film elongation-at-break around 320%, and a dry film modulus of 4.5 MPa, and a dry film strength of 25 Mpa, and a dry film elongation-at-break around 59%.

Example 5

Preparation of Filled Capsules

5a. The wet films of Example 2 were used to form capsules using a manual press, and a vegetable oil was used as an example filling. First, the film was placed on a heated metal with a small cavity, and a vacuum was used to conform the wet film to the cavity surface. The oil was then added quickly to fill the cavity. Another wet film was placed on the top. Finally, a heated metal piece was used to press against the bottom metal piece. A capsule was formed and removed from the press. The manual press was kept at 45-75° C.

5b. A capsule was formed the same as in 5a except, the moisture in the wet film was decreased. The sealability was improved and the capsule was stronger.

Example 6

Preparation of a Ribbon

Long ribbons were produced using a roller-coater with a temperature-controlled sample feeder. The ribbons were cast on a polyethylene terephthalate (PET) substrate, with a single sided release liner. The film went through a drying tunnel to allow removing the moisture.

6a. The made ribbons were fed directly into a capsule machine to form capsules.

6b. The dried ribbons were stored for later use. Remoisturizing, such as running the film through a water steam, was helpful in providing the film enough flexibility for encapsulation after storage.

Example 7

Properties of the Capsules

The capsules can be made into different sizes and shapes using different dies on a capsule machine using drum coaters.

The capsules were clear and had a slightly translucency. The dried capsules were stable for at least six months and the capsules gave reasonable dissolution in both water and gastric fluid.

We claim:

1. A soft capsule shell comprising:
   (a) a gum consisting essentially of a high acyl gellan gum having more than 40% acetyl and more than 45% glyceryl residual substitutents per repeat unit and a low acyl gellan gum having less than 25% acetyl and less than 15% glyceryl residual substitutents per repeat unit wherein the high acyl gellan gum is present in an amount of from about 0.3 to about 5% and the low acyl gellan gum is present in an amount of from about 0.1 to about 4% by weight of the composition on a wet basis;
   (b) a starch; and
   (c) a plasticizer, wherein the plasticizer is in an amount of from 30 to 80% of the starch (w/w dry basis).

2. The capsule of claim 1, wherein the ratio of high acyl gellan to low acyl gellan is from about 0.25:1.0 to about 30.0:1.0.

3. The capsule of claim 1, wherein the starch contains at least about 10% by weight amylose.

4. The capsule of claim 3, wherein the starch is a stabilized starch selected from the group consisting of a hydroxypropylated starch, a hydroxyethylated starch, an acetylated starch, and mixtures thereof.

5. The capsule of claim 1, wherein the starch is a dextrinized starch.

6. The capsule of claim 1, wherein the starch is present in an amount of from about 15% to about 40%, by weight of the composition on a wet film basis.

7. The capsule of claim 2, wherein the starch is present in an amount of from about 15% to about 40%, by weight of the composition on a wet film basis.

8. The capsule of claim 4, wherein the starch is present in an amount of from about 15% to about 40%, by weight of the composition on a wet film basis.

9. The capsule of claim 1, wherein the plasticizer is glycerin and is present in an amount of from about 30 to 80% by weight of the starch.

10. The capsule of claim 1, wherein the plasticizer is glycerin and is present in an amount of from about 30 to 80% by weight of the starch.

11. The capsule of claim 2, wherein the plasticizer is glycerin and is present in an amount of from about 30 to 80% by weight of the starch.

12. The capsule of claim 1, further comprising 6 hydrophilic or surface hydrophilically modified colloidal particles.

13. The capsule of claim 1, further comprising hydrophilic or surface hydrophilically modified colloidal particles.

14. The capsule of claim 2, farther comprising hydrophilic or surface hydrophilically modified colloidal particles.

15. The capsule shell of claim 1, wherein the ratio of high acyl gellan to low acyl gellan is from about 0.25:1.0 to about 30.0:1.0.

16. The capsule shell of claim 15, wherein the starch is contains at least about 10% by weight amylose and is selected from the group consisting of a hydroxypropylated starch, a hydroxyetbylated starch, an acetylated starch, and mixtures thereof

17. The capsule shell of claim 1, wherein the starch has a water fluidity of from about 20 to 90.

* * * * *